US00PP17615P2

(12) United States Plant Patent
Murakami et al.

(10) Patent No.: US PP17,615 P2
(45) Date of Patent: Apr. 17, 2007

(54) ***CALIBRACHOA* PLANT NAMED 'SUNBELKURIHO'**

(50) Latin Name: ***Calibrachoa* sp.**
Varietal Denomination: Sunbelkuriho

(75) Inventors: Yasuyuki Murakami, Shiga (JP); Takeshi Kanaya, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/259,303

(22) Filed: Oct. 26, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Calibrachoa* plant named 'Sunbelkuriho', characterized by its outwardly spreading, trailing and decumbent plant habit; vigorous growth habit; freely branching habit; freely flowering habit; long flowering period; white-colored flowers; and good weather tolerance.

1 Drawing Sheet

Botanical designation: *Calibrachoa* sp.
Cultivar denomination: 'Sunbelkuriho'.

BACKGROUND OF THE INVENTION

The present Invention relates to a new and distinct cultivar of *Calibrachoa* plant, botanically known as *Calibrachoa* sp., and hereinafter referred to by the cultivar name 'Sunbelkuriho'.

The new *Calibrachoa* is a naturally-occurring branch mutation of the *Calibrachoa* sp. cultivar Sunbelbura, disclosed in U.S. Plant Pat. No. 14,405. The new *Calibrachoa* was discovered and selected by the Inventors in a controlled environment in Higashiomi, Shiga, Japan in September, 2002.

Asexual reproduction of the new cultivar by terminal cuttings in a controlled environment in Higashiomi, Shiga, Japan since April, 2003, has shown that the unique features of this new *Calibrachoa* are stable and reproduced true to type in successive generations.

SUMMARY OF THE INVENTION

Plants of the cultivar Sunbelkuriho have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Sunbelkuriho'. These characteristics in combination distinguish 'Sunbelkuriho' as a new and distinct cultivar of *Calibrachoa:*

1. Outwardly spreading, trailing and decumbent plant habit.
2. Vigorous growth habit.
3. Freely branching habit.
4. Freely flowering habit.
5. Long flowering period.

6. White-colored flowers.
7. Good weather tolerance; tolerant to rain and low and high temperatures.

Plants of the new *Calibrachoa* differ primarily from plants of the parent, the cultivar Sunbelbura, in flower color as plants of the cultivar Sunbelbura have red purple-colored flowers.

Plants of the new *Calibrachoa* can be compared to plants of the cultivar Sunbelkuho, disclosed in U.S. Plant Pat. No. 10,278. In side-by-side comparisons conducted in Higashiomi, Shiga, Japan, plants of the new *Calibrachoa* were broader and had smaller leaves than plants of the cultivar Sunbelkuho. In addition, plants of the new *Calibrachoa* had larger flowers than plants of the cultivar Sunbelkuho.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Calibrachoa.*

The photograph at the top of the sheet comprises a side perspective view of a typical flowering plant of 'Sunbelkuriho' grown in a container.

The photograph at the bottom of the sheet is a close-up view of typical flowers and leaves of 'Sunbelkuriho'.

DETAILED BOTANICAL DESCRIPTION

In the following description, color references are made to The Royal Horticultural Society Colour Chart, 2001 Edition, except where general terms of ordinary dictionary significance are used. Plants grown in 25-cm containers for about seven months were used for the aforementioned photographs and following description. Plants were grown under conditions which closely approximate commercial production conditions during the summer in Higashiomi, Shiga, Japan in an outdoor nursery. During the production period, day temperatures were about 25° C. and night temperatures were about 15° C. Plants were pinched one time in the spring.

Botanical classification: *Calibrachoa* sp. cultivar Sunbelkuriho.

Parentage: Naturally-occurring branch mutation of the *Calibrachoa* sp. cultivar Sunbelbura, disclosed in U.S. Plant Pat. No. 14,405.

Propagation:

*Type cutting.*—Terminal vegetative cuttings.

*Time to initiate roots.*—About one week at 20° C. to 25° C.

*Time to produce a your rooted plant.*—About three weeks at 20° C. to 25° C.

*Root description.*—Fine, fibrous, fleshy; light brown in color.

*Rooting habit.*—Freely branching.

Plant description:

*Plant form and growth habit.*—Annual flowering plant; outwardly spreading, trailing and decumbent plant habit. Vigorous growth habit.

*Plant height.*—About 14 cm.

*Plant diameter.*—About 56 cm.

*Branching habit.*—Freely branching, about 150 lateral branches potentially develop per plant; pinching enhances lateral branch development.

*Lateral branch description.*—Length: About 20.4 cm. Diameter: About 1.3 mm. Internode length: About 9 mm. Texture: Pubescent. Color: 144B.

*Foliage description.*—Arrangement: Alternate; simple. Length: About 2.4 cm. Width: About 6 mm. Shape: Oblanceolate. Apex: Rounded. Base: Cuneate. Margin: Entire. Texture, upper and lower surfaces: Pubescent. Venation pattern: Pinnate; reticulate. Color: Developing and fully expanded foliage, upper surface: 137C; venation, close to 144C. Developing and fully expanded foliage, lower surface: 138D; venation, close to 144C. Petiole length: About 1.9 mm. Petiole diameter: About 0.6 mm. Petiole texture, upper and lower surfaces: Pubescent. Petiole color, upper and lower surfaces: 144D.

Flower description:

*Flower type and habit.*—Flowers face upright or outward; single, axillary; salverform. Flowers not persistent. Freely flowering habit, numerous flowers per plant, about two flowers develop per lateral branch. Flowers not fragrant.

*Natural flowering season.*—Spring to late autumn in Japan; flowering continuous during this period.

*Time to flower.*—Early flowering; plants begin flowering about three to four weeks after planting.

*Flower longevity on the plant.*—About seven to ten days.

*Flower size.*—Diameter: About 3.1 cm. Depth: About 2.3 cm. Throat diameter (distal): About 8 mm. Tube diameter (proximal): About 2.2 mm.

*Flower buds.*—Length: About 2.2 cm. Diameter: About 4.6 mm. Shape: Elongated oblong. Color: 145C; towards the apex, N155B.

*Corolla.*—Arrangement/appearance: Singe whorl of five petals fused into flared trumpet. Petal length from throat: About 1.1 cm. Petal width: About 1.3 cm. Petal shape: Spatulate. Petal apex: Rounded. Petal margin: Entire. Petal texture, upper and lower surfaces: Smooth, glabrous; satiny. Color: Petal, when opening, upper and lower surfaces: N155B. Petal, fully opened, upper and lower surfaces: N155B. Flower throat (inside): 7A. Flower tube (outside): 151D.

*Sepals.*—Arrangement/appearance: Single whorl of five sepals fused at base; star-shaped calyx. Length: About 1 cm. Width: About 2.3 mm. Shape: Lanceolate. Apex: Acute. Margin: Entire. Texture, upper and lower surfaces: Pubescent. Color, upper and lower surfaces: 144A.

*Peduncles.*—Length: About 1.1 cm. Width: About 0.5 mm. Strength: Moderately strong. Texture: Pubescent. Color: 144B.

*Reproductive organs.*—Stamens: Quantity: Five per flower. Anther shape: Ellipsoidal. Anther length: About 0.8 mm. Anther color: 4C. Pollen amount: Scarce. Pollen color: 13C. Pistils: Quantity: One per flower. Pistil length: About 7 mm. Stigma shape: Ellipsoidal. Stigma color: 144B. Style length: About 5 mm. Style color: 144D. Ovary color: 144D.

*Seeds.*—Seed development has not been observed.

Disease/pest resistance: Plants of the new *Calibrachoa* have not been noted to be resistant to pathogens and pests common to *Calibrachoas.*

Weather/temperature tolerance: Plants of the new *Calibrachoa* are tolerant to rain and wind and have been observed to tolerate temperatures from 0° C. to 35° C.

It is claimed:

1. A new and distinct cultivar of *Calibrachoa* plant named 'Sunbelkuriho', as illustrated and described.

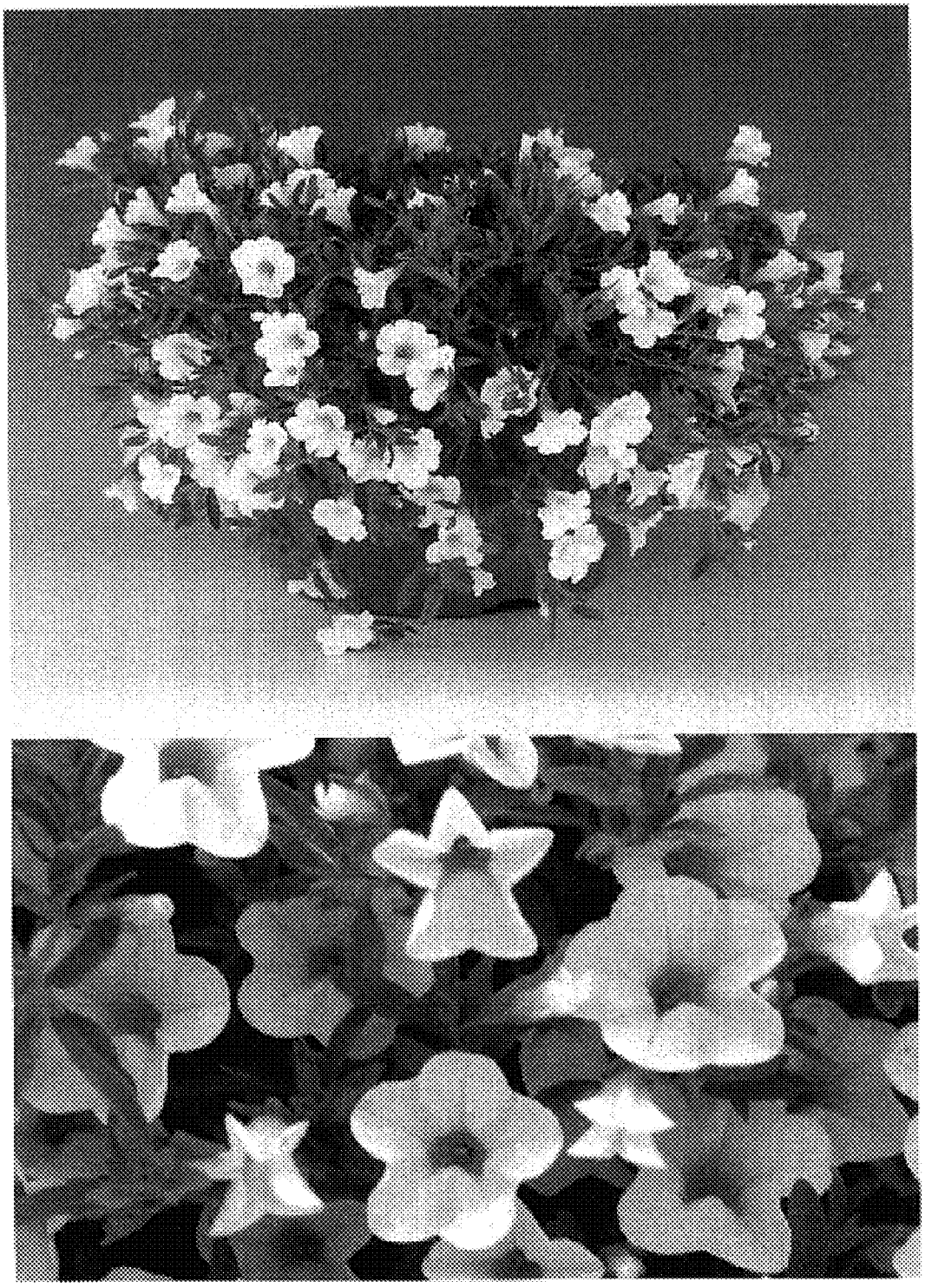

* * * * *